US010025903B2

United States Patent
Li et al.

(10) Patent No.: US 10,025,903 B2
(45) Date of Patent: Jul. 17, 2018

(54) VALIDATING A METADATA TREE USING A METADATA INTEGRITY VALIDATOR

(75) Inventors: Jun Li, Mountain View, CA (US); Ram Swaminathan, Cupertino, CA (US); Sharad Singhal, Belmont, CA (US)

(73) Assignee: ENTIT SOFTWARE, LLC, Sanford, NC (US)

( * ) Notice: Subject to any disclaimer, the term of this patent is extended or adjusted under 35 U.S.C. 154(b) by 0 days.

(21) Appl. No.: 14/421,734

(22) PCT Filed: Sep. 12, 2012

(86) PCT No.: PCT/US2012/054881
§ 371 (c)(1),
(2), (4) Date: Feb. 13, 2015

(87) PCT Pub. No.: WO2014/028038
PCT Pub. Date: Feb. 20, 2014

(65) Prior Publication Data
US 2015/0242641 A1  Aug. 27, 2015

Related U.S. Application Data

(60) Provisional application No. 61/683,702, filed on Aug. 15, 2012, provisional application No. 61/683,705, filed on Aug. 15, 2012.

(51) Int. Cl.
*G06F 21/60* (2013.01)
*G06F 17/30* (2006.01)
(Continued)

(52) U.S. Cl.
CPC ...... *G06F 19/322* (2013.01); *G06F 17/30109* (2013.01); *G06F 17/30327* (2013.01);
(Continued)

(58) Field of Classification Search
CPC ............... G06F 17/30; G06F 17/30002; G06F 17/30005; G06F 17/30008; G06F 17/30997; G06F 21/602; G06F 19/322; G06F 21/64
See application file for complete search history.

(56) References Cited

U.S. PATENT DOCUMENTS 6,968,456 B1 * 11/2005 Tripathi ............... G06F 21/64
707/999.009
7,181,017 B1  12/2007 Nagal et al.
(Continued)

FOREIGN PATENT DOCUMENTS

CN  101976322  2/2011
JP  H08-163488  6/1996
(Continued)

OTHER PUBLICATIONS

Kundu et al., "On Hashing Graphs", Jun. 20, 2012, IBM T J Watson Research Center—Department of Computer Science and CERIAS, Purdue University, p. 1 and 11-12.*
(Continued)

*Primary Examiner* — Samson Lemma
*Assistant Examiner* — Arya Golriz

(57) ABSTRACT

A method performed by a processing system includes reconstructing a metadata tree of a patient from a metadata tree journal, the metadata tree including a plurality of references to a corresponding plurality of encrypted electronic health records of the patient in an encrypted data store, and validating the metadata tree by comparing first integrity information of the metadata tree to second integrity information corresponding to the metadata tree journal provided by a metadata integrity validator.

18 Claims, 10 Drawing Sheets

(51) Int. Cl.
  *G06F 19/00* (2018.01)
  *G06F 21/64* (2013.01)
  *G06Q 50/24* (2012.01)
  *G06Q 10/10* (2012.01)
  *H04L 29/06* (2006.01)
  *G16H 10/60* (2018.01)

(52) U.S. Cl.
  CPC ...... *G06F 17/30997* (2013.01); *G06F 21/602* (2013.01); *G06F 21/64* (2013.01); *G06Q 10/10* (2013.01); *G06Q 50/24* (2013.01); *G16H 10/60* (2018.01); *H04L 63/0457* (2013.01); *H04L 63/064* (2013.01); *G06Q 2220/10* (2013.01)

(56) References Cited

U.S. PATENT DOCUMENTS

| | | | |
|---|---|---|---|
| 7,587,368 | B2 | 9/2009 | Felsher |
| 7,702,640 | B1 | 4/2010 | Vermeulen et al. |
| 8,041,749 | B2 | 10/2011 | Beck |
| 8,176,018 | B1 | 5/2012 | Bisson et al. |
| 2002/0194209 | A1 | 12/2002 | Bolosky et al. |
| 2003/0074564 | A1 | 4/2003 | Peterson |
| 2005/0256742 | A1 | 11/2005 | Kohan et al. |
| 2006/0028488 | A1* | 2/2006 | Gabay ............... H04L 29/06027 345/626 |
| 2006/0129435 | A1 | 6/2006 | Smitherman et al. |
| 2006/0184554 | A1* | 8/2006 | Albert ............... G06F 17/30265 |
| 2006/0277076 | A1* | 12/2006 | Hasan ............... G06F 19/322 705/3 |
| 2007/0294317 | A1 | 12/2007 | Christy et al. |
| 2008/0065661 | A1 | 3/2008 | Mazzagatti et al. |
| 2009/0006346 | A1* | 1/2009 | C N ............... G06F 17/30454 |
| 2009/0271408 | A1 | 10/2009 | Goetz |
| 2011/0001605 | A1 | 1/2011 | Kiani et al. |
| 2011/0119089 | A1 | 5/2011 | Carlisle |
| 2013/0227285 | A1* | 8/2013 | Bracher ............... G06F 21/62 713/168 |

FOREIGN PATENT DOCUMENTS

| | | |
|---|---|---|
| JP | 2002-543497 | 12/2002 |
| JP | 2004-192639 | 7/2004 |
| JP | 2004-326358 | 11/2004 |
| JP | 2005-539423 | 12/2005 |
| JP | 2008-509477 | 3/2008 |
| JP | 2009-519511 | 5/2009 |
| JP | 2011-118550 | 6/2011 |
| JP | 2011-198020 | 10/2011 |
| KR | 1020020026284 A | 4/2002 |
| WO | WO-2010149333 | 12/2010 |

OTHER PUBLICATIONS

Bessani, A et al, "Depsky: Dependable and Secure Storage in a Cloud-of-Clouds", Apr. 10-13, 2011, Univ of Lisbon.

International Search Report and Written Opinion of the International Searching Authority, dated Mar. 18, 2013; issued in related PCT Application No. PCT/US2012/054881.

Li, M, "User-centric Security and Privacy Mechanisms in Untrusted Networking and Computing Environments", Jul. 2011.

International Search Report and Written Opinion of the International Searching Authority, dated Mar. 18, 2013; issued in related PCT Application No. PCT/US2012/054885.

Kyosuke Yasuda and Takao Miura, "Distributed Processes on Tree Hash Under Concurrency Control", The Institute of Electronics, Information and Communication Engineers (IEICE), Proceedings of the 19th Data Engineering Workshop, Japan, IEICE Data Engineering Event Stream, Apr. 7, 2008, DEW2008 D2-2.

Sujoy Basu, et al., "Fusion: Managing Healthcare Records at Cloud Scale", Computer, USA, IEEE, Aug. 22, 2012, vol. 45, Issue 11, pp. 42-49.

Takuya Kitano and Misa Miura, "An XML Document Management System using a Setnistructured Data Model", Proceedings of the 57th annual conference of IPSJ(3), Japan, Information Processing Society of Japan. Oct. 5, 1998, 5V-5, p. 3-23-3-284.

* cited by examiner

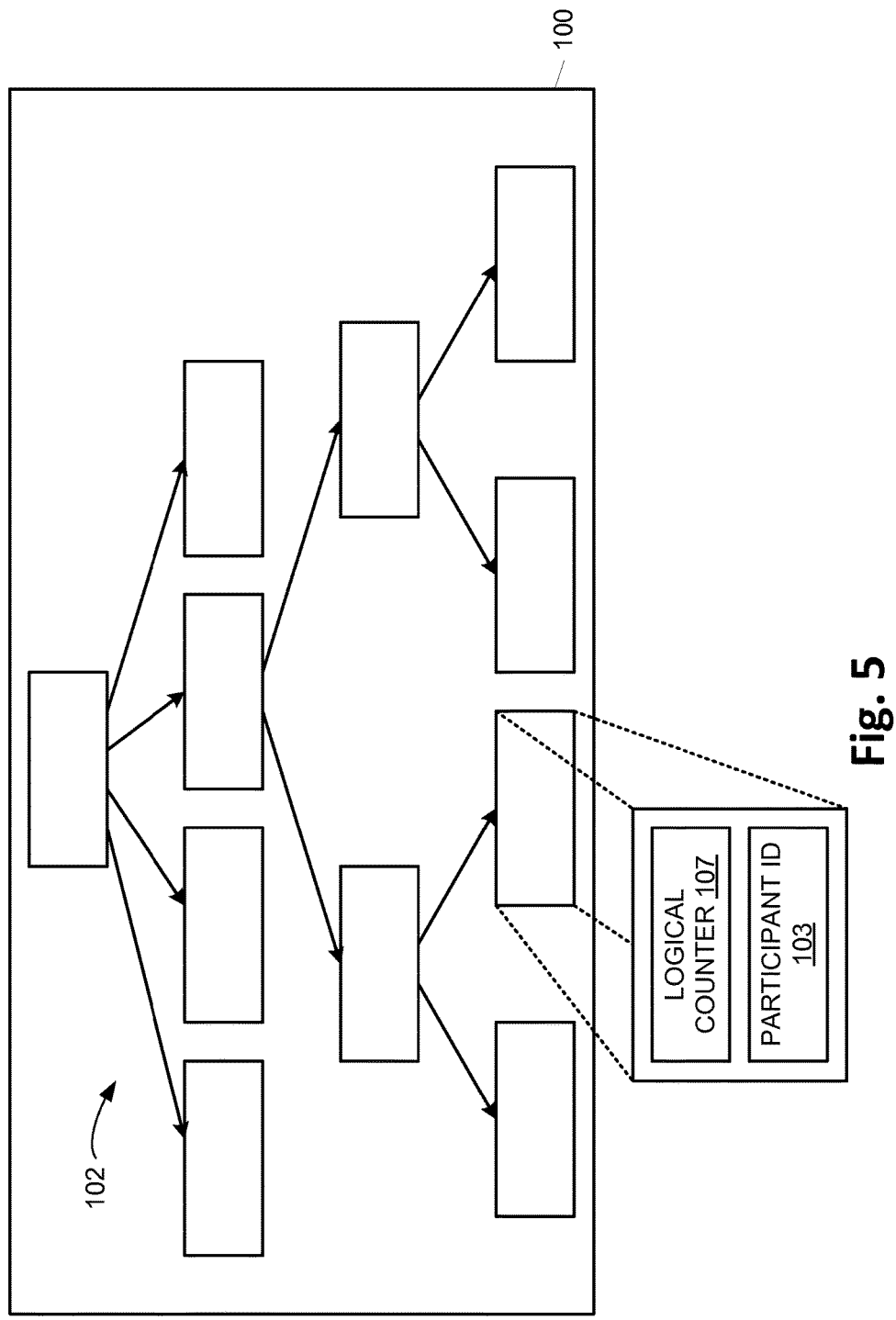

VALIDATING A METADATA TREE USING A METADATA INTEGRITY VALIDATOR

CROSS REFERENCE TO RELATED APPLICATIONS

This application claims priority to U.S. Provisional Patent Application No. 61/683,702, entitled "Protocols for Reading and Writing Electronic Medical Data Asynchronously in an Untrusted Cloud Storage", and filed Aug. 15, 2012 and U.S. Provisional Patent Application No. 61/683,705, entitled "Metadata Tree Journaling with Access Right Revocation in an Electronic Medical Cloud Data Store", and filed Aug. 15, 2012. The disclosures of these applications are incorporated by reference herein.

BACKGROUND

Electronic Health Records (EHRs) may enable healthcare participants (e.g., patients, healthcare providers, payers, and researchers) to improve coordination of care and access to health information. Although EHRs may facilitate access to healthcare information, the sharing of healthcare information may involve many complex technical and legal issues. The technical issues may include how to provide concurrent access to different participants and how to revoke access of participants as needed. These issues may be burdensome for healthcare participants that lack the resources and expertise to enable such sharing while ensuring consistency, privacy, and security of the healthcare information.

BRIEF DESCRIPTION OF THE DRAWINGS

FIG. 5 is a block diagram illustrating one example of a metadata summary tree.

DETAILED DESCRIPTION

Figure 1A:
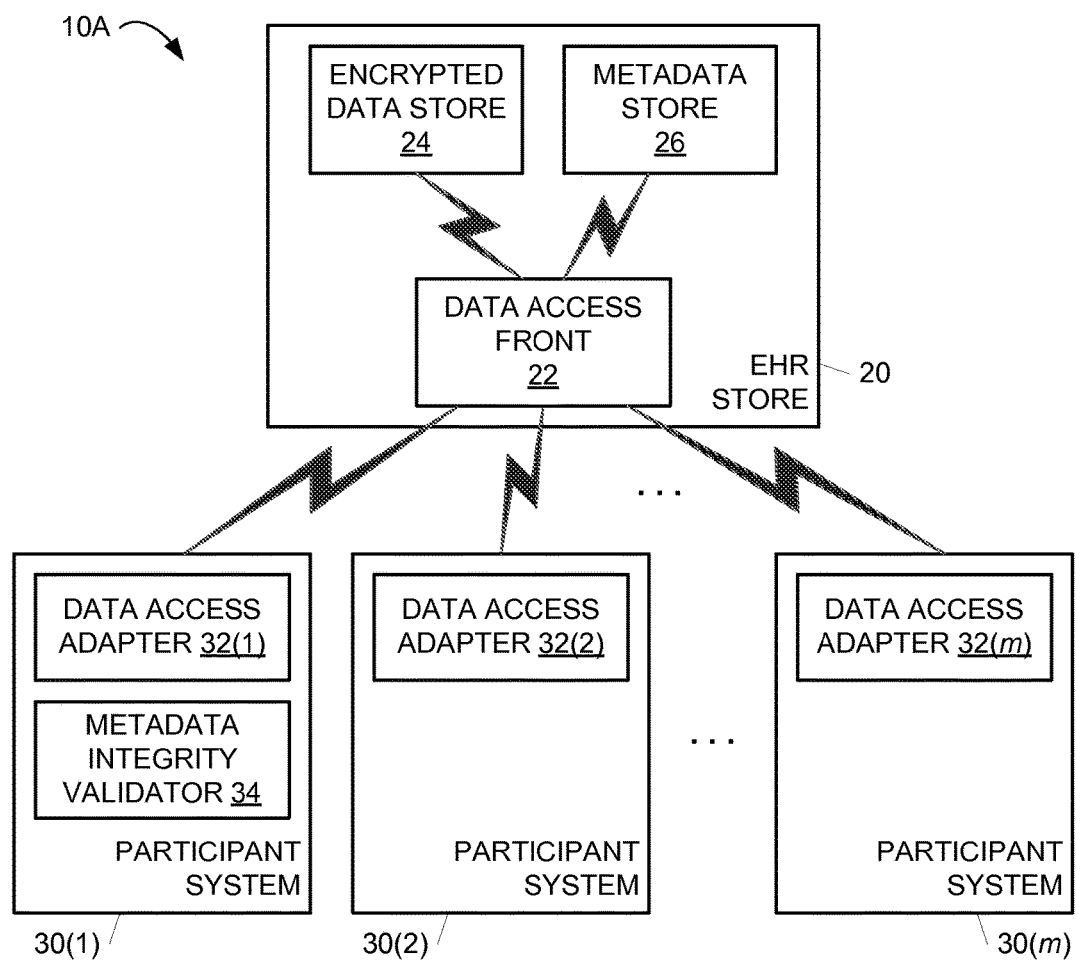
FIGS. 1A-1C are block diagrams illustrating examples of electronic health record store processing environments.

In the following detailed description, reference is made to the accompanying drawings, which form a part hereof, and in which is shown by way of illustration specific embodiments in which the disclosed subject matter may be practiced. It is to be understood that other embodiments may be utilized and structural or logical changes may be made without departing from the scope of the present disclosure. The following detailed description, therefore, is not to be taken in a limiting sense, and the scope of the present disclosure is defined by the appended claims.

Embodiments described herein provide an electronic health record (EHR) store processing environment that enables secure, seamless sharing of EHRs among healthcare participants (e.g., patients, healthcare providers, payers, and researchers). The environment includes an encrypted data store that stores encrypted EHRs of patients and a metadata tree store that stores a metadata tree journal for each patient. Each metadata tree journal may be used to reconstruct a metadata tree of a corresponding patient that provides a mapping to the EHRs of the patient in the encrypted data store. The metadata tree journal for each patient may be accessed by authorized healthcare participants, such as healthcare providers, to allow the participants to access and store EHRs of patients.

The environment also includes a metadata integrity validator to support concurrent read and write accesses to a metadata tree journal of a patient. The metadata integrity validator stores integrity information for a metadata tree that represents the committed state of the metadata tree. Healthcare participant systems use the integrity information to ensure that a consistent and most up-to-date version of a metadata tree is reconstructed from the metadata tree journal.

The metadata store stores each metadata tree journal using a journaling mechanism that provides a storage framework that is append-only and immutable. A healthcare participant system accesses the metadata tree journal of a patient from the metadata store, reconstructs the metadata tree using the journal and integrity information from the validator, and validates the reconstructed metadata tree using the integrity information. Using a validated metadata tree, the healthcare participant system accesses encrypted EHRs from and/or stores EHRs to the encrypted data store. When storing encrypted EHRs, the healthcare participant system also updates the metadata tree journal on the metadata store using the journaling mechanism and updates the integrity information on the validator.

The environment controls access to EHRs using record keys for encrypted EHRs, node keys for the nodes of metadata trees, and metadata tree keys for the structure of metadata trees. Healthcare participants that store encrypted EHRs in the encrypted data store encrypt the EHRs using record keys. These participants also add nodes for the corresponding encrypted EHRs to the metadata tree. The nodes include references to the corresponding encrypted EHRs that are encrypted with corresponding node keys. The structure of a metadata tree is also encrypted using a metadata tree key to limit access to the metadata tree to authorized healthcare participants of a patient with the metadata tree key.

One or more healthcare participants may manage different subtrees of the metadata tree of a patient. To manage a subtree, a participant manages the node keys of the corresponding nodes in the subtree to grant and revoke access to other authorized healthcare participants of a patient. A participant grants access by providing selected node and record keys to another participant. A participant revokes access by rotating the node keys and embedding revocation information into corresponding nodes of the metadata tree. After a key revocation, a participant whose access has been revoked will not be able to access encrypted EHRs that are stored after the revocation or store new encrypted EHRs to the encrypted data store. The revoked participant will, however, continue to be able to access encrypted EHRs that were stored prior to the revocation.

As used herein, the term "healthcare participant" (also referred to as "participant") refers to a patient, a healthcare provider, a payer, a researcher, or other suitable person involved in a healthcare process of a patient that generates and/or uses healthcare information corresponding to a patient. The term "patient" refers to a person that receives at least one healthcare service from a healthcare provider. The term "healthcare provider" (also referred to as "provider") refers to a person and/or institution that provides at least one healthcare service to a patient.

The term "electronic health record" (EHR) refers to a set of healthcare information generated by a healthcare participant and stored in an electronic format on at least one machine-readable storage medium. The term "encrypted electronic health record" refers to an electronic health record that has been encrypted with a record key.

The term "metadata" refers to a set of information that describes at least one record, such as an electronic health record. The term "metadata tree" refers to a set of nodes that includes metadata where each node has a specified relationship with at least one other node in the set. The term "metadata tree journal" refers to a data structure created by an append-only, immutable journaling mechanism for storing the nodes of metadata trees.

The term "record key" refers to an encryption key that is used to encrypt and decrypt an EHR of a patient. The term "node key" refers to an encryption key that is used to encrypt and decrypt a portion of a node in a metadata tree of a patient. The term "metadata tree key" refers to an encryption key that is used to encrypt and decrypt at least a portion of a metadata tree of a patient.

FIG. 1A is a block diagram illustrating one example 10A of an electronic health record store processing environment 10. Environment 10A includes electronic health record (EHR) store 20 and a set of healthcare participant systems 30(1)-30(m) where m is an integer that is greater than or equal to two. Environment 10A provides the ability to create, access, store, manage, and share EHRs of patients using EHR store 20 and participant systems 30.

EHR store 20 includes a data access front 22, an encrypted data store 24, and a metadata store 26. Data access front 22 communicates with participant systems 30 to manage accesses to encrypted data store 24 and metadata store 26. Encrypted data store 24 stores encrypted EHRs of patients that were generated and provided by participant systems 30. The encrypted EHRs are encrypted and decrypted by participant systems 30 using record keys. Encrypted data store 24 includes any suitable type, number, and/or configuration of machine-readable storage media to store the encrypted EHRs. Because the EHRs are encrypted and because encrypted data store 24 does not store the encryption keys (i.e., record keys) for the EHRs, encrypted data store 24 may or may not be a trusted data store (e.g., encrypted data store 24 may be owned or operated by one or more untrusted third parties).

Metadata store 26 stores a metadata tree journal (e.g., metadata tree journal 60 shown in FIG. 2) for each patient that was generated and provided by one or more authorized participant systems 30. Metadata store 26 implements a journaling mechanism to provide a storage framework for the metadata tree journals, where the journaling mechanism is append-only and immutable. As will be described in additional detail below, each metadata tree journal may be used by a participant system 30 to reconstruct a metadata tree (e.g., metadata tree 70 shown in FIG. 2) of a corresponding patient that provides a mapping to the EHRs of the patient in encrypted data store 24.

Figure 2:
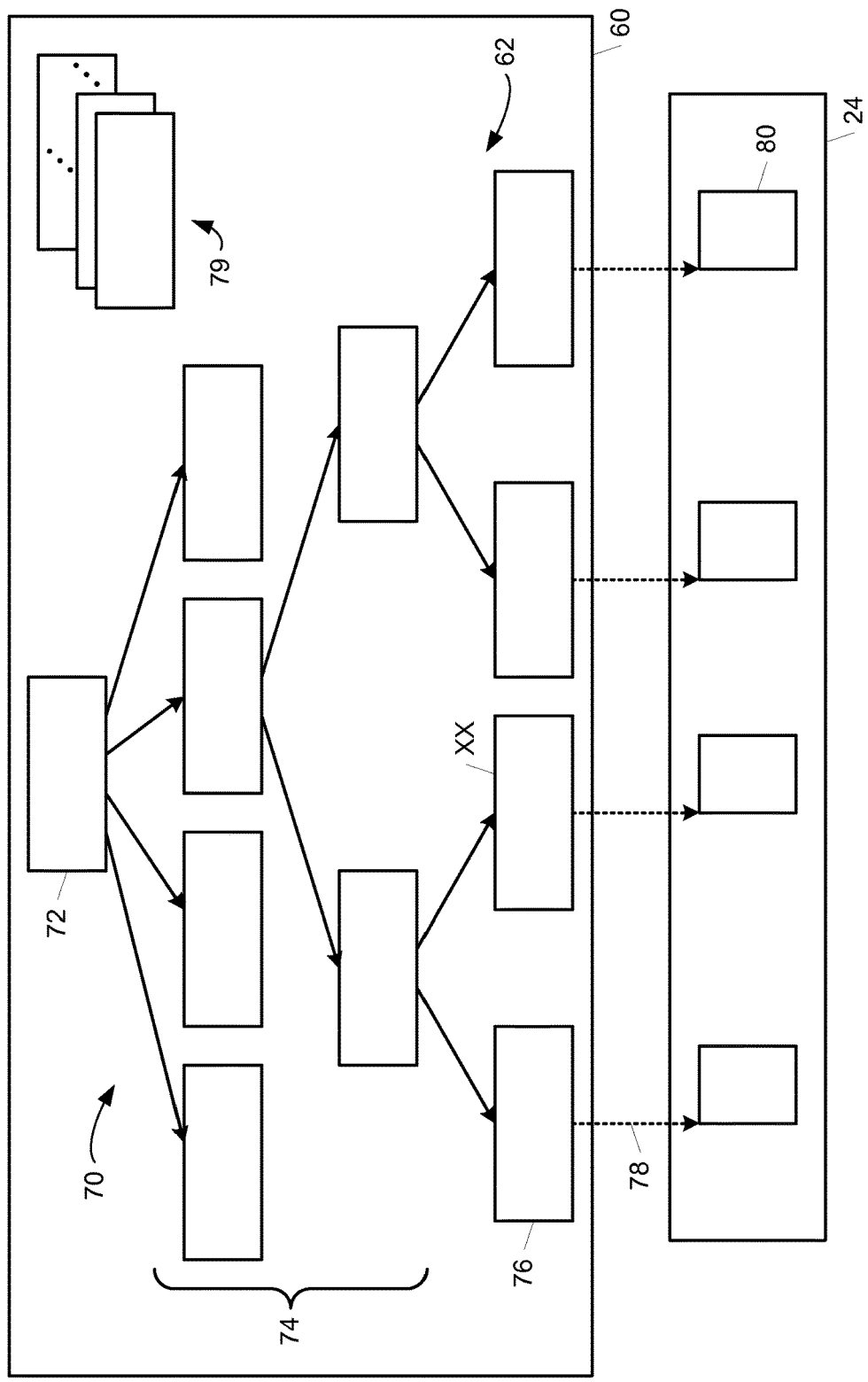
FIG. 2 is a block diagram illustrating one example of a metadata tree journal and encrypted electronic health records in an encrypted data store.

FIG. 2 is a block diagram illustrating one example of metadata tree journal 60 and encrypted electronic health records 80 in encrypted data store 24. Metadata tree journal 60 includes nodes 62, where nodes 62 include committed nodes 72, 74, and 76 and uncommitted nodes 79. Committed nodes 72, 74, and 76 collectively form metadata tree 70, which may be reconstructed by a participant system 30. Metadata tree 70 represents a hierarchical tree structure with a root node 72, any number of intermediate nodes 74, and a leaf node 76 for a corresponding encrypted EHR 80. Root node 72 may include information that identifies the patient, intermediate nodes 74 represent logical groupings of EHRs 80 (e.g., by provider or by categories of patient information such as treatment conditions), and leaf nodes 76 include a reference 78 to a corresponding encrypted EHR 80 in encrypted data store 24. References 78 are used by participant systems 30 to access encrypted EHRs 80 in encrypted data store 24.

Figure 3:
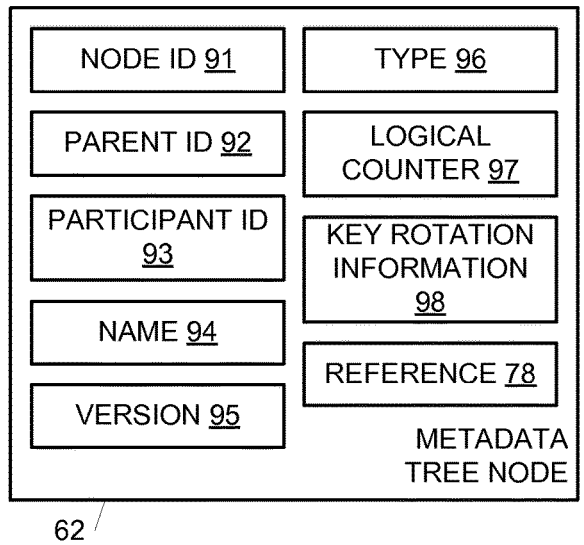
FIG. 3 is a block diagram illustrating one example of a metadata tree node.

FIG. 3 is a block diagram illustrating one example of a metadata tree node 62. Metadata tree node 62 includes a node identifier 91, a parent identifier 92, a participant identifier 93, a name 94, a version 95, a type 96, a logical counter 97, key rotation information 98, and a reference 78. Node identifier 91 is a globally unique identifier for node 62, and parent identifier 92 is a node identifier 91 of a parent node of node 62. Participant identifier 93 is information that identifies the healthcare participant that created node 62. Name 94 is a name given the healthcare participant that created node 62. Version 95 is a version number of node 62. Type 96 is a type of node 62 such as new, updated, or key revocation. Logical counter 97 is a counter value that represents the number order of node 62 under the parent node (e.g., the logical counter 97 of the i-th leaf node 76 under an intermediate node 74 (i.e., a parent node of leaf node 76) would be i). Key rotation information 98 includes information that may be used to identify revoked node keys of any child nodes of node 62. Reference 78 identifies a location of encrypted EHRs 80 in encrypted data store 24.

As referred to herein, a metadata tree node 62 designated with a type 96 of new will be referred to as a new node 62. A metadata tree node 62 designated with a type 96 of updated will be referred to as an updated node 62, and a metadata tree node 62 designated with a type 96 of key revocation will be referred to as a revocation node 62.

In other examples of metadata tree node 62, other suitable information such as a time stamp, a digital signature of the healthcare participant that created node 62, and a digital signature of the healthcare participant that created an encrypted EHR 80 corresponding to node 62 may be stored in metadata tree node 62.

The journaling mechanism implemented by metadata store 26 allows unaffiliated providers (e.g., providers practicing under different, unrelated business entities) to concurrently store updates to metadata store 26. The append-only and immutability characteristics of the journaling ensure that, when a node 62 is updated, metadata tree journal 60 stores both the original node 62 and an updated node 62.

Figure 4A:
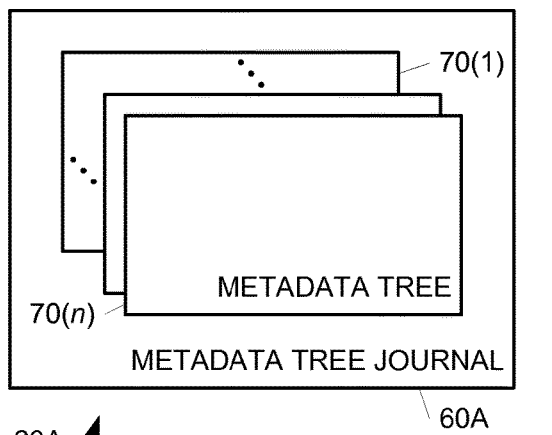
FIGS. 4A-4B are block diagrams illustrating examples of metadata tree journals.
Figure 4B:
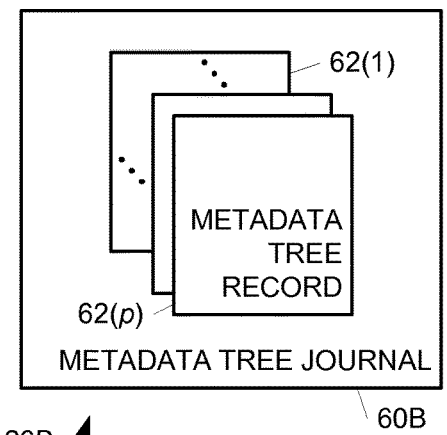

Metadata store 26 may implement any suitable type of journaling mechanism, such as full metadata tree journaling as shown in the example of FIG. 4A or incremental metadata tree journaling as shown in the example of FIG. 4B.

In the example of FIG. 4A, metadata store 26A implements full metadata tree journaling where every write operation performed by a participant system 30 stores the entire updated metadata tree 70 to a metadata tree journal 60A in metadata store 26A. Thus, as shown in FIG. 4A, a first write operation stores an entire metadata tree 70(1) with an additional node 62 for the write operation to metadata tree journal 60A. Similarly, the n-th write operation stores an entire metadata tree 70(n) with an additional node 62 for the write operation to metadata tree journal 60A.

In the example of FIG. 4B, metadata store 26B implements incremental metadata tree journaling where every write operation performed by a participant system 30 stores an additional node 62 for the write operation to a metadata tree journal 60B in metadata store 26B without re-storing the nodes 62 previously stored in journal 60B. Thus, as shown in FIG. 4B, a first write operation stores an additional node 62(1) for the write operation to metadata tree journal 60B. Similarly, the p-th write operation stores an additional node 62(P) for the write operation to metadata tree journal 60B.

Referring back to FIG. 1A, the structural portions of each metadata tree 70 (i.e., at least node identifier 91, parent identifier 93, and participant identifier 94 in each node 62 of each tree 70) stored by metadata store 26 are encrypted using a metadata tree key. This metadata tree encryption allows environment 10A to limit access to a metadata tree 70 of a patient to authorized healthcare participants of the patient with the metadata tree key. The metadata tree key may be a patient-specific key that is generated by the patient. The metadata tree key may, for example, be provided to a healthcare participant when a patient registers with the participant or provided from one healthcare participant (e.g., a primary care physician) to another healthcare participant (e.g., a consulting physician).

Other portions of each metadata tree 70 (i.e., at least reference 78 in each node 62) are further encrypted with node keys by participant systems 30 that generate the nodes 62. This node key encryption prevents unauthorized healthcare participants from obtaining references 78 to encrypted EHRs in encrypted data store 24 and therefore prevents unauthorized healthcare participants from accessing the encrypted EHRs from encrypted data store 24. The node keys may be participant-specific keys that are generated by participants. A node key may be provided from a healthcare participant that stores an encrypted EHR 80 and the corresponding node 76 in metadata tree 70 to another healthcare participant to allow the other healthcare participant to decrypt the reference 78 in node 76 and thereby locate the encrypted EHR 80 in encrypted data store 24.

Participants, including patients, healthcare providers, payers, researchers, and other suitable persons involved in healthcare processes of patients, (not shown) interact with corresponding participant systems 30 to communicate with EHR store 20 using corresponding data access adapters 32 to create, access, store, manage, and share EHRs of patients. Each data access adapter 32 communicates with data access front 22 on EHR store 20 to access encrypted data store 24 and metadata store 26.

Environment 10A also includes a metadata integrity validator 34 implemented on participant system 30(1) to support concurrent read and write accesses to metadata tree journal 60 of a patient. Metadata integrity validator 34 stores integrity information 150 (shown in FIG. 7) for metadata tree 70 that represents the committed state of metadata tree 70. Participant systems 30 use integrity information 150 accessed from metadata integrity validator 34 to ensure that a consistent and most up-to-date version of metadata tree 70 is reconstructed from metadata tree journal 60. Thus, metadata integrity validator 34 ensures that read and write accesses to encrypted data store 24 are performed by participant systems 30 based on a valid version of metadata tree 70.

Integrity information 150 includes a hash and a metadata summary tree (shown as metadata summary tree 100 in FIG. 5) of the most recently committed metadata tree in metadata tree journal 60. The hash and summary are generated by a participant system 30 as part of the process of storing an encrypted EHR to encrypted data store 24 and adding a corresponding node 62 to a metadata tree 70. Because the hash and the metadata summary tree in integrity information 150 represent the committed state of metadata tree 70, the hash will also be referred to as the committed hash and the metadata summary tree will also be referred to as the committed metadata summary tree.

The hash in integrity information 150 may be generated as a function of an in-order traversal of metadata tree 70, where the in-order traversal is determined using the logical counter 97 of each node 62 in metadata tree 70. In one example, the hash may be generated as a function of the entire in-order traversal of metadata tree 70.

In another example, starting with root node 72 (referred to as RootNode in Equation 2), an initial value of $H_{current}$ may be computed as a function of the hash of root node 72 using Equation 1.

$$H_{current} = \text{Hash}(\text{RootNode}) \quad \text{Equation 1}$$

An in-order traversal of tree 70 is then performed using logical counters 97 where, at each node 74 and 76 (referred to as CurrentNode in Equation 2), the value $H_{current}$ is updated using Equation 1.

$$H_{current} = \text{Hash}(\text{Hash}(\text{CurrentNode}) \| H_{current}) \quad \text{Equation 2}$$

After the hash of the last node 74 or 76 of the traversal is included into $H_{current}$, the final $H_{current}$ records the hash of the entire metadata tree 70.

Metadata summary tree 100 in integrity information 150 records an ordering of nodes 62 of metadata tree 70 based on logical counters 97 as shown in the example of FIG. 5. Each node 102 in metadata summary tree 100 corresponds to a node 62 in metadata tree 70 and includes copies 107 and 103 of the logical counter 97 and the participant identifier 93, respectively, of the corresponding node 62.

Figure 1B:
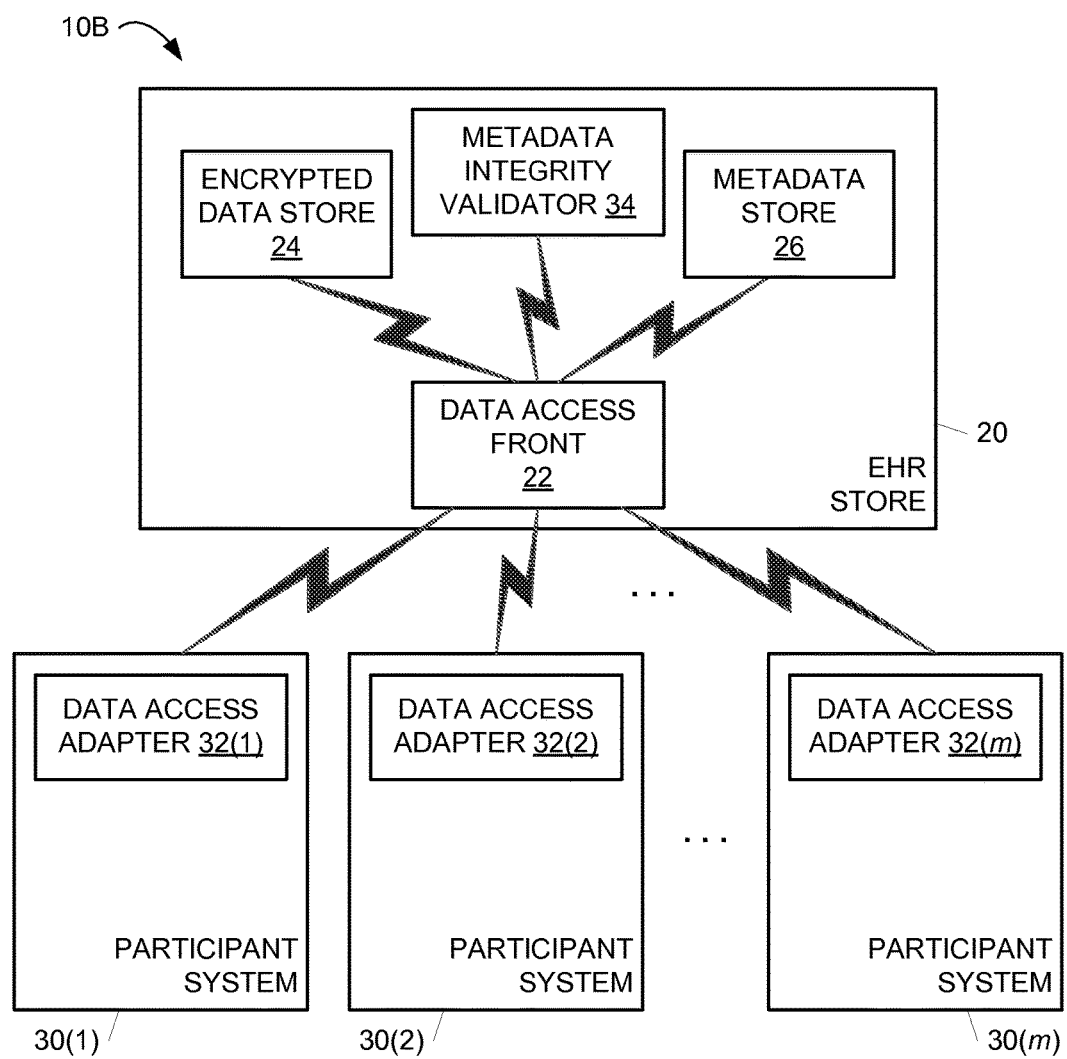

In environment 10A, participant systems 30 access integrity information 150 from and provide integrity information 150 to metadata integrity validator 34 on participant system 30(1). Participant system 30(1) may, for example, correspond to a primary care physician of a patient or other participant with a relationship to the patient. In another example 10B of environment 10 shown in FIG. 1B, participant systems 30 access integrity information 150 from and provide integrity information 150 to metadata integrity validator 34 through data access front 22.

Figure 1C:
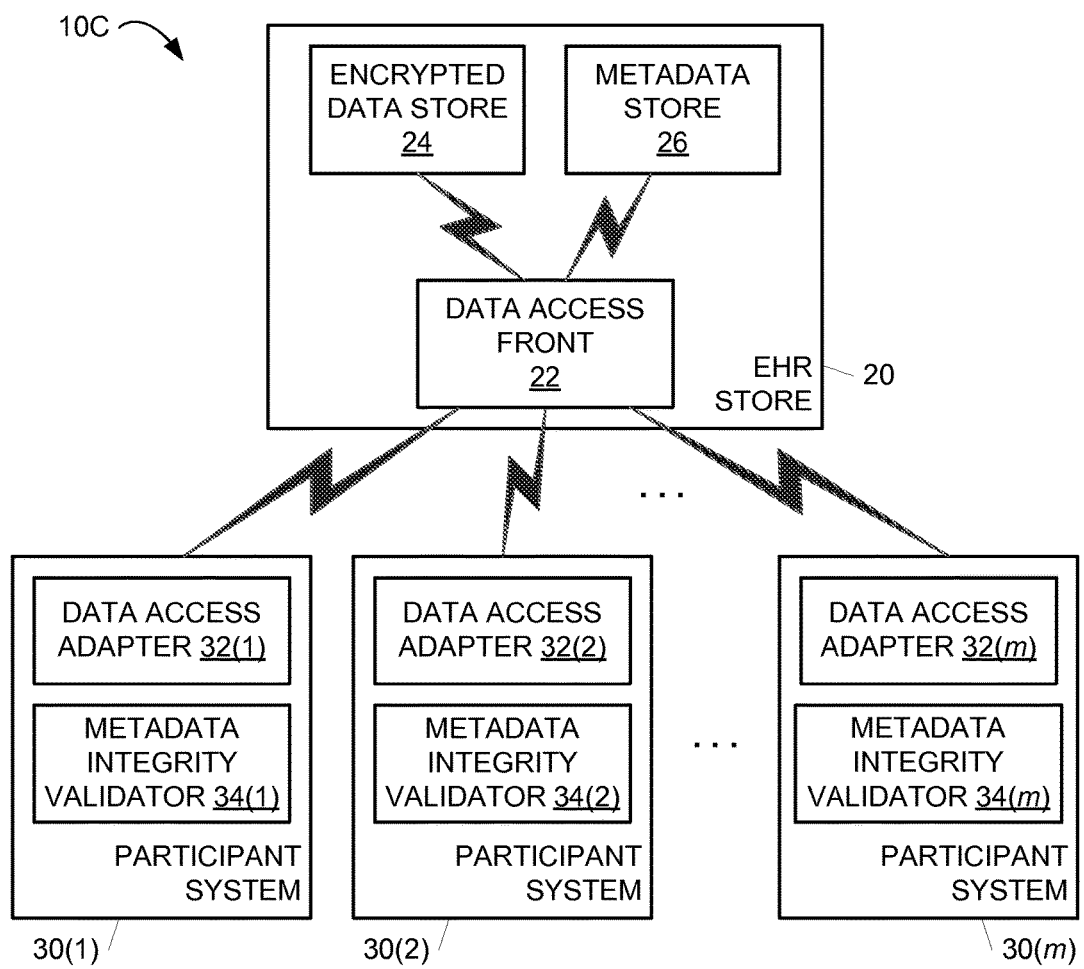

In a further example 10C of environment 10 shown in FIG. 1C, metadata integrity validator 34 may be distributed across two or more participant systems 30 as metadata integrity validators 34(1)-34(m). In this example, each metadata integrity validator 34(1)-34(m) stores a hash and a metadata summary tree for a corresponding subtree of metadata tree 70 that is managed by the corresponding participant of the participant system 30. The hash and metadata summary may be generated as described above using the in-order traversal of the corresponding subtree, rather than the entire metadata tree 70.

As described in additional detail below with reference to FIGS. 6-9, participant system 30 accesses metadata tree journal 60 of a patient from metadata store 26, reconstructs metadata tree 70 using journal 60 and integrity information 150 from metadata integrity validator 34, and validates the reconstructed metadata tree 70 using integrity information 150. Using the validated metadata tree 70, participant system 30 accesses encrypted EHRs 80 from and/or stores EHRs 80 to encrypted data store 24. When storing encrypted EHRs 80, participant system 30 also updates metadata tree journal 60 on metadata store 26 using the journaling mechanism and updates integrity information 150 on metadata integrity validator 34.

Figure 6:
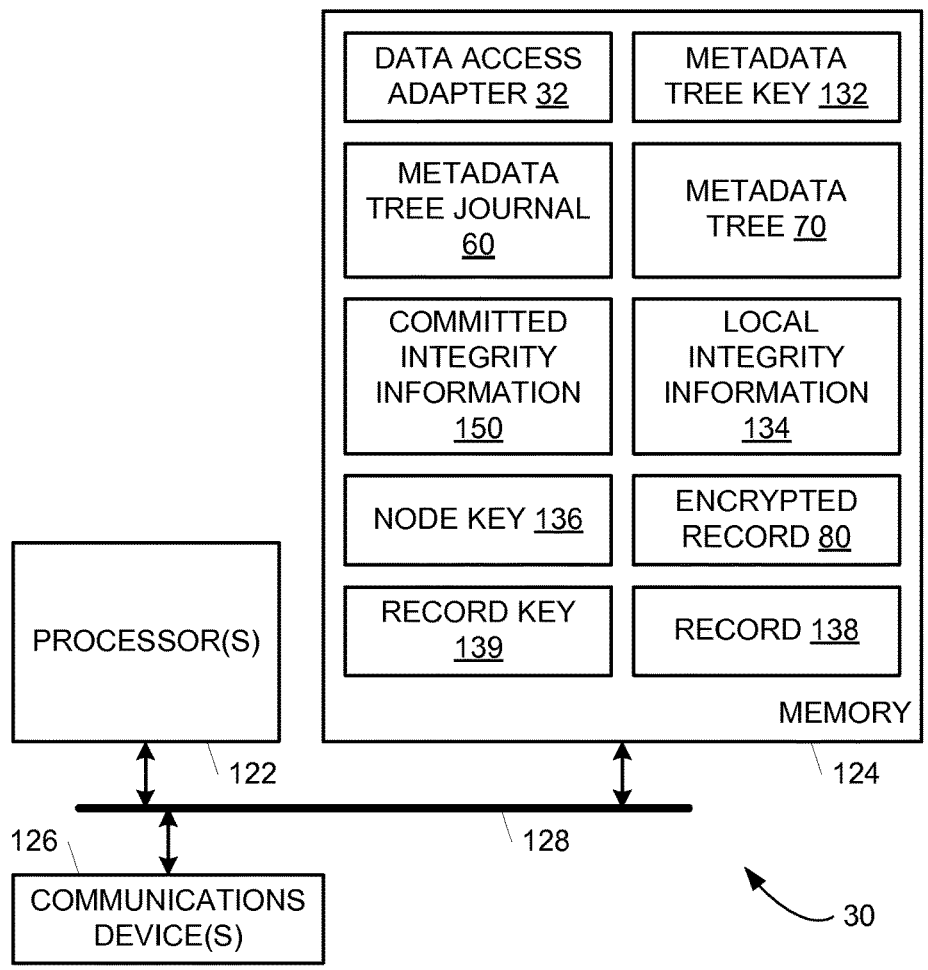
FIG. 6 is a block diagram illustrating one example of a healthcare participant system.

Environment 10, EHR store 20 and participant systems 30, may be implemented with any suitable type, number, and configuration of processing systems that each include one or more processors for executing instructions stored in one or more memories. In particular, data access front 22, encrypted data store 24, and metadata store 26 may be implemented using different processing systems in some embodiments. An example of participant system 30 is shown in FIG. 6 and described in additional detail below. In addition, any suitable type, number, and configuration of wired and/or wireless network devices (not shown) may be used to allow the processing systems to communicate.

FIG. 6 is a block diagram illustrating one example of healthcare participant system 30. Participant system 30 includes a set of one or more processors 122 configured to execute a set of instructions stored in a memory system 124, memory system 124, and at least one communications device 126. Processors 122, memory system 124, and communications devices 126 communicate using a set of interconnections 128 that includes any suitable type, number, and/or configuration of controllers, buses, interfaces, and/or other wired or wireless connections.

Participant system 30 represents any suitable processing device or portion of a processing device such as a server computer, a laptop computer, a tablet computer, a desktop computer, a mobile telephone with processing capabilities (i.e., a smart phone), or another suitable type of electronic device with processing capabilities. Each processor 122 is configured to access and execute instructions stored in memory system 124 and to access and store data in memory system 124. Memory system 124 includes any suitable type, number, and configuration of volatile or non-volatile machine-readable storage media configured to store instructions and data. Examples of machine-readable storage media in memory system 124 include hard disk drives, random access memory (RAM), read only memory (ROM), flash memory drives and cards, and other suitable types of magnetic and/or optical disks. The machine-readable storage media are considered to be part of an article or article of manufacture. An article or article of manufacture refers to one or more manufactured components. Communications devices 126 include any suitable type, number, and/or configuration of communications devices configured to allow participant system 30 to communicate across one or more wired or wireless networks.

Figure 7:
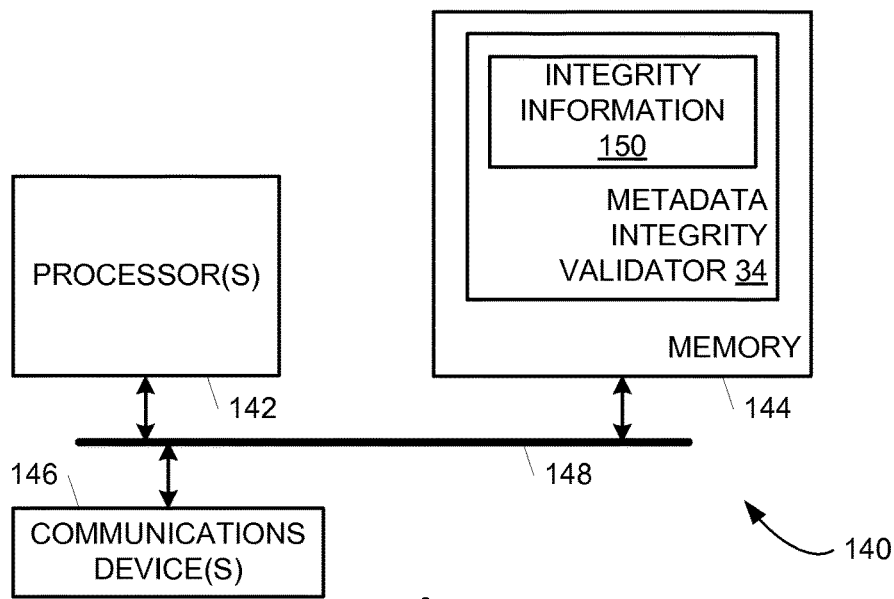
FIG. 7 is a block diagram illustrating one example of a metadata integrity validator system.

FIG. 7 is a block diagram illustrating one example of a metadata integrity validator system 140 that implements metadata integrity validator 34. Metadata integrity validator system 140 includes a set of one or more processors 142 configured to execute a set of instructions stored in a memory system 144, memory system 144, and at least one communications device 146. Processors 142, memory system 144, and communications devices 146 communicate using a set of interconnections 148 that includes any suitable type, number, and/or configuration of controllers, buses, interfaces, and/or other wired or wireless connections and are structured and operate as described above for processors 122, memory system 124, and communications devices 126, respectively.

As noted above with reference to FIGS. 1A-1C, metadata integrity validator system 140 may be integrated with a single participant system 30 as shown in FIG. 1A, may be separate from participant systems 30 as shown in FIG. 1B, or may be distributed across two or more participant systems 30 as shown in FIG. 1C.

Referring back to FIG. 6, data access adapter 32 includes instructions that, when executed by processors 122, causes processors 122 to perform the functions of data access adapter 32 that will be now described with reference to FIGS. 8-10.

Figure 8:
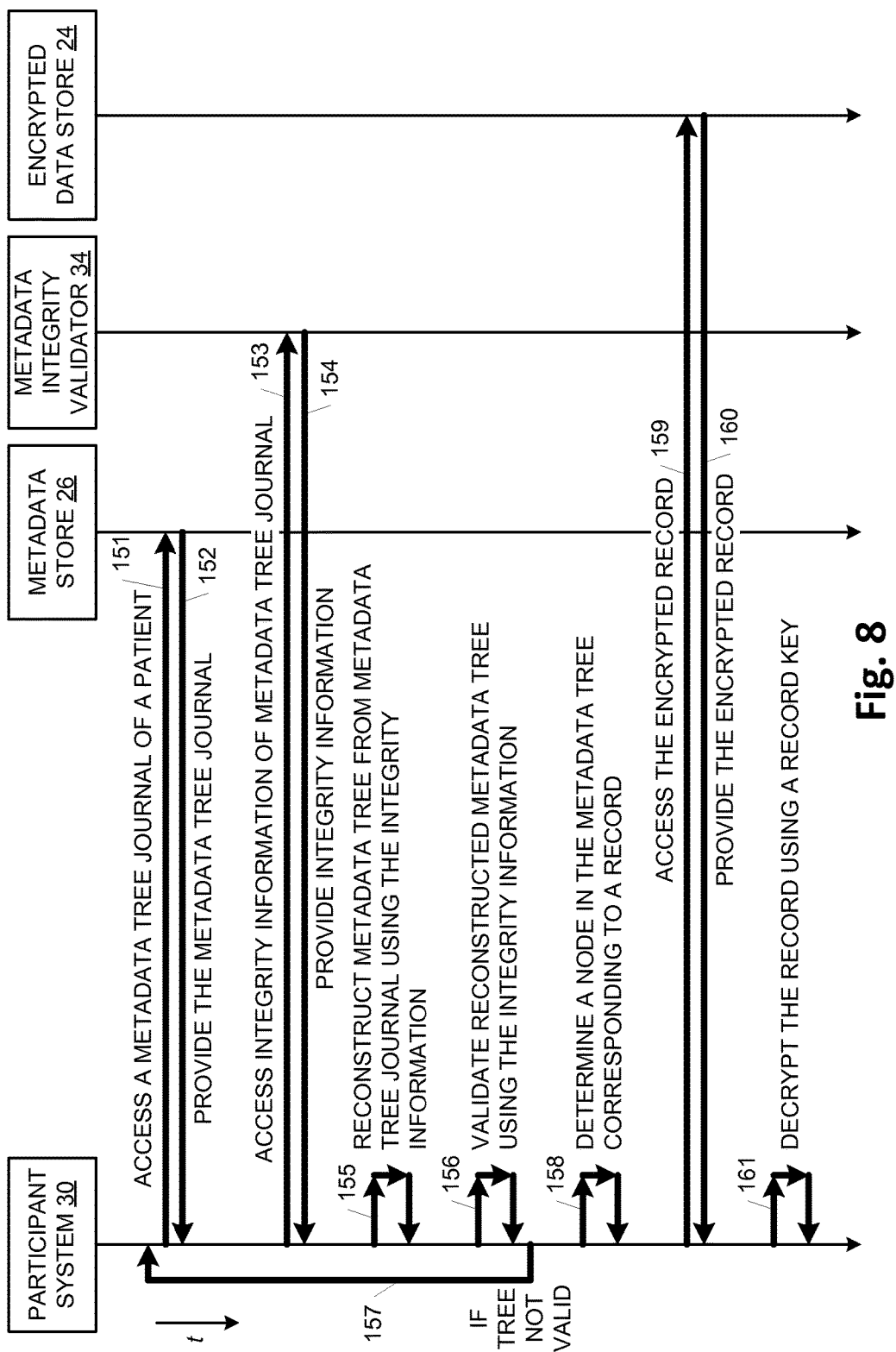
FIG. 8 is a schematic diagram illustrating one example of accessing an encrypted electronic health record using a metadata tree in a concurrent processing environment.

FIG. 8 is a schematic diagram illustrating one example of accessing an encrypted EHR 80 using a metadata tree 70(n) or 70 in a concurrent processing environment. Referring to FIGS. 6 and 8, data access adapter 32 accesses metadata tree journal 60 of patient 12 from metadata store 26 through data access front 22 as indicated by an arrow 151. Metadata store 26 provides metadata tree journal 60 to participant system 30 through data access front 22 as indicated by an arrow 152. In embodiments with full metadata tree journaling as shown in FIG. 4A, metadata tree journal 60 provided by metadata store 26 includes the most recent full metadata tree 70(n). In embodiments with incremental metadata tree journaling as shown in FIG. 4B, metadata tree journal 60 provided by metadata store 26 includes all of the nodes 62 that were stored in metadata tree journal 60.

Data access adapter 32 accesses integrity information 150 of metadata tree journal 60 from metadata integrity validator 34 as indicated by an arrow 153. Metadata integrity validator 34 provides integrity information 150 to participant system 30 as indicated by an arrow 154.

Data access adapter 32 reconstructs metadata tree 70 from metadata tree journal 60 using integrity information 150 as indicated by an arrow 155. In embodiments with full metadata tree journaling shown in FIG. 4A, data access adapter 32 decrypts the most recent full metadata tree 70(n) using metadata tree key 132. Data access adapter 32 reconstructs metadata tree 70(n) from an in order traversal and removes any uncommitted nodes 62 identified using the metadata summary tree 100 (shown in FIG. 5). Data access adapter 32 identifies uncommitted nodes 62 as those nodes 62 whose logical counter 97 and participant identifier 93 do not match the logical counter 107 and participant identifier 103 in a corresponding node 102 in metadata summary tree 100. For example, if two nodes 62 with the same logical counter 97 appear in metadata tree 70(n), data access adapter 32 removes the node 62 whose participant identifier 103 in a corresponding node 102 in metadata summary tree 100 does not match.

In embodiments with incremental metadata tree journaling shown in FIG. 4B, data access adapter 32 decrypts all of the nodes 62 from metadata tree journal 60 using metadata tree key 132 and reconstructs metadata tree 70 with all nodes 62 using an in order traversal. Data access adapter 32 removes any uncommitted nodes 62 whose logical counter 97 and participant identifier 93 do not match the logical counter 107 and participant identifier 103 in a corresponding node 102 in metadata summary tree 100. For example, if two nodes 62 with the same logical counter 97 appear in the full metadata tree 70, data access adapter 32 removes the node 62 whose participant identifier 103 in a corresponding node 102 in metadata summary tree 100 does not match.

Data access adapter 32 validates the reconstructed metadata tree 70 using integrity information 150 as indicated by an arrow 156. After removing uncommitted nodes 62 from the reconstructed metadata tree 70(n) or 70, data access adapter 32 generates local integrity information 134 which includes a local hash of metadata tree 70(n) or 70 (e.g., a hash of an in-order traversal of metadata tree 70(n) or 70 as described in the example above) and compares the local hash to the committed hash from integrity information 150. If the local hash differs from the committed hash, then data access adapter 32 determines that the reconstructed tree 70(n) or 70 is not valid (i.e., not the most consistent or most up-to-date metadata tree in metadata tree journal 60) and repeats the functions of arrows 151-156 as indicated by an arrow 157. For example, a write to metadata tree journal could occur between the times that the functions of arrows 151 and 153 occur. Once the local hash is the same as the committed hash, then data access adapter 32 determines that the reconstructed tree 70(n) or 70 is valid.

Data access adapter 32 determines a node 76 in the reconstructed metadata tree 70(n) or 70 corresponding to an encrypted EHR 80 as indicated by an arrow 158. Data access adapter 32 decrypts the node 76 using a node key 136 that may have been generated within participant system 30 as part of storing node 76 in metadata tree journal 60 or provided to participant system 30 by another participant system 30 that stored the node 76 in metadata tree journal 60. By decrypting node 76, data access adapter 32 decrypts reference 78 from node 76 to allow a desired encrypted EHR 80 to be accessed from encrypted data store 24.

Data access adapter 32 accesses the encrypted EHR 80 from encrypted data store 24 through data access front 22 as indicated by an arrow 159. Encrypted data store 24 provides the desired encrypted EHR 80 through data access front 22 as indicated by an arrow 160. Data access adapter 32 stores the encrypted EHR 80 and decrypts encrypted EHR 80 into a decrypted EHR 138 using a record key 139 as indicated by an arrow 161. Record key 139 may have been generated within participant system 30 as part of storing encrypted EHR 80 in encrypted data store 24 or provided to participant system 30 by another participant system 30 that stored the encrypted EHR 80 in encrypted data store 24. Data access adapter 32 may display or otherwise output decrypted EHR 138 to the participant.

Figure 9:
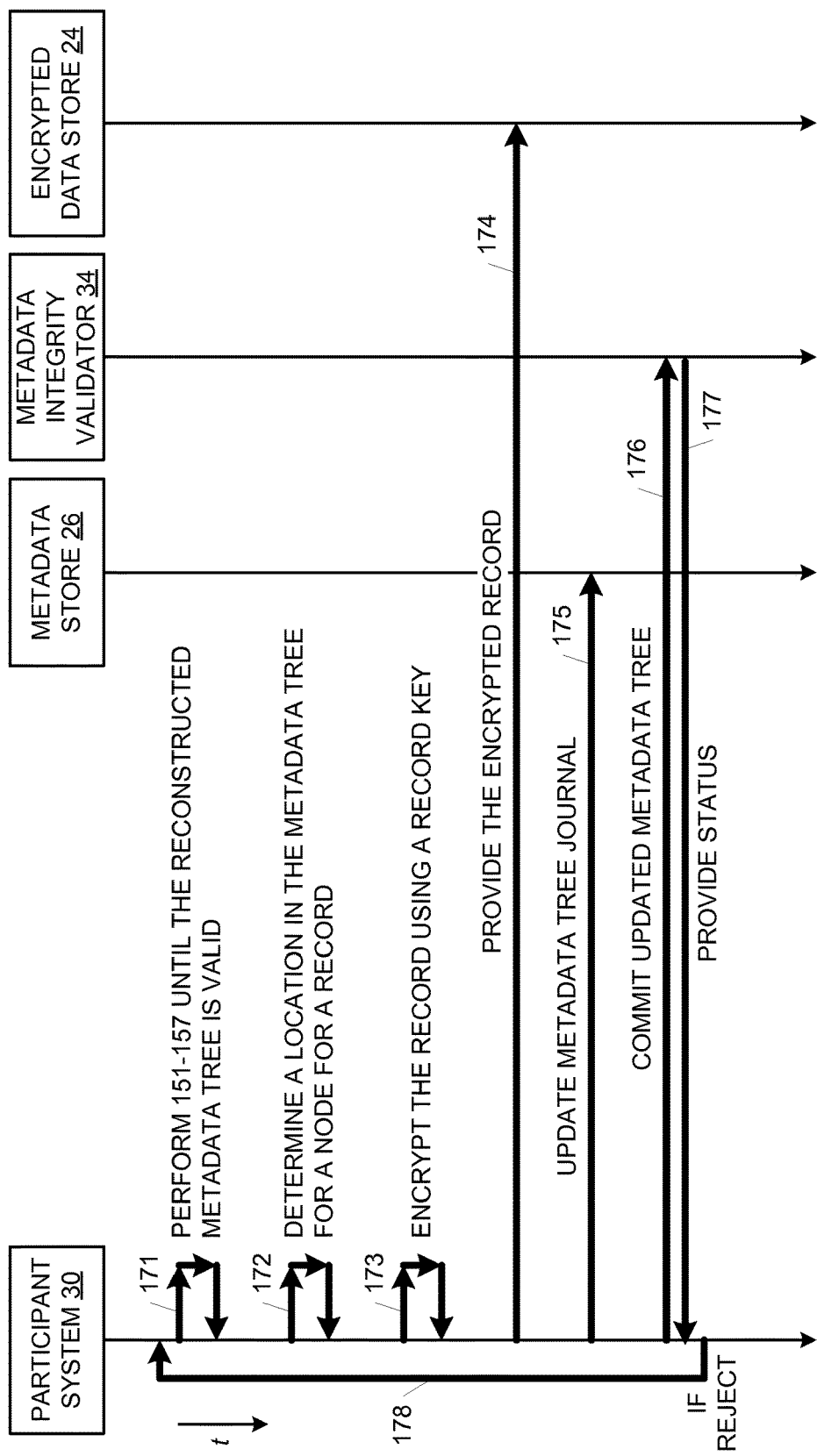
FIG. 9 is a schematic diagram illustrating one example of storing an encrypted electronic health record using a metadata tree in a concurrent processing environment.

FIG. 9 is a schematic diagram illustrating one example of storing an encrypted EHR 80 using a metadata tree 70(n) or 70 in a concurrent processing environment. Referring to FIGS. 6, 8, and 9, data access adapter 32 performs the functions of arrows 151-157 of FIG. 8 until the reconstructed metadata tree 70(n) or 70 is valid as indicated by an arrow 171. Data access adapter 32 determines location in metadata tree 70(n) or 70 for a node 76 for an EHR 138 as indicated by an arrow 172.

Data access adapter 32 encrypts EHR 138 into encrypted EHR 80 using record key 139 as indicated by an arrow 173. Record key 139 may be generated by participant system 30 as part of storing encrypted EHR 80 in encrypted data store 24 or provided to participant system 30 by another participant system 30 that manages the subtree of metadata tree 70(n) or 70 that includes node 76.

Data access adapter 32 provides encrypted EHR 80 to encrypted data store 24 through data access front 22 as indicated by an arrow 174. Data access adapter 32 updates metadata tree journal 60 in metadata store 26 through data access front 22 as indicated by an arrow 148.

In embodiments with full metadata tree journaling as shown in FIG. 4A, data access adapter 32 updates metadata tree journal 60 by creating a node 76 with a reference 78 to the stored encrypted EHR 80 and adding node 76 to metadata tree 70(n) to form an updated metadata tree 70(N+1). Data access adapter 32 encrypts node 76 with node key 136, encrypts updated metadata tree 70(N+1) with metadata tree key 132, and provides the encrypted, updated metadata tree 70(N+1) to metadata tree journal 60 in metadata store 26.

In embodiments with incremental metadata tree journaling as shown in FIG. 4B, data access adapter 32 updates metadata tree journal 60 by creating a node 76 with a reference 78 to the stored encrypted EHR 80 and encrypting node 76 with node key 136. Data access adapter 32 provides the encrypted node 76 to metadata store 26, without providing metadata tree 70, to append the encrypted node 76 to metadata tree journal 60. Data access adapter 32 also adds node 76 to metadata tree 70 to allow local integrity information 134 to be generated for the updated metadata tree 70.

With both full and incremental metadata tree journaling, data access adapter 32 may generate node key 136 as part of updating metadata tree journal 60 or may receive node key 136 from another participant system 30 that manages the subtree in metadata tree 70(n) where node 76 is added.

Data access adapter 32 attempts to commit the updated metadata tree 70(N+1) or 70 to metadata integrity validator 34 as indicated by an arrow 176. To do so, data access adapter 32 generates local integrity information 134 for metadata tree 70(N+1) or 70 which includes a hash of metadata tree 70(N+1) or 70 (e.g., a hash of an in-order traversal of metadata tree 70(N+1) or 70 as described in the example above) and a metadata summary tree 100 of metadata tree 70(N+1) or 70. Data access adapter 32 provides local integrity information 134 along with the committed hash from committed integrity information 150 to metadata integrity validator 34.

In response to receiving local integrity information 134 and the committed hash from data access adapter 32, metadata integrity validator 34 compares the committed hash from data access adapter 32 to the committed hash stored in committed integrity information 150 on metadata integrity validator 34. If the hash from data access adapter 32 matches the hash stored on metadata integrity validator 34, then metadata integrity validator 34 commits the local integrity information 134 to committed integrity information 150 on metadata integrity validator 34 and provides a success status to data access adapter 32 as indicated by an arrow 177.

If the hash from data access adapter 32 does not match the hash stored on metadata integrity validator 34, then metadata integrity validator 34 does not commit the local integrity information 134 to committed integrity information 150 on metadata integrity validator 34 and provides a rejected status to data access adapter 32. For example, another participant system 30 may have committed a different updated metadata tree 70(N+1) or 70 to metadata tree journal 60 between the times that the functions of arrows 171 and 176 occur. Data access adapter 32 repeats the functions of arrows 171-177 as indicated by an arrow 178 until the updated metadata tree 70(N+1) or 70 is successfully committed by metadata integrity validator 34.

In the above examples, data access adapter 32 may include a logging service to record the read and write progress of each read and write of metadata store 26 performed by data access adapter 32. If data access adapter 32 becomes inoperable (e.g., crashes) while performing a read or write operation to metadata store 26, data access adapter 32 accesses the log to resume any unfinished read or write operations when it becomes operable.

As noted above different participants may manage different subtrees of metadata tree 70 using different participant systems 30. To manage a subtree, a participant manages the node keys of the corresponding nodes 74 and 76 in the subtree to grant and revoke access to other authorized healthcare participants of a patient. A participant grants access by providing selected node and record keys to another participant. A participant revokes access by rotating the node keys and embedding revocation information into corresponding nodes of the metadata tree.

To revoke access of other participants to a subtree of metadata tree 70, data access adapter 32 embeds key revocation information into metadata tree 70 by updating key rotation information 98 in a parent node 74 of the subtree (e.g., by adding a hash of the revoked node key to key rotation information 98) and adding a revocation node 76 (i.e., a node with type 96 set to key revocation) under the parent node 74. Data access adapter 32 uses functions 171 and 175-178 shown in FIG. 9 and described above to update a metadata tree journal 60 with the updated parent node 74 and the revocation node 76 and commit the updated metadata tree 70(N+1) or 70.

After a key revocation, a participant who does not have an updated node key will not be able to access encrypted EHRs 80 corresponding to the subtree that are stored to encrypted data store 24 after the revocation or store new encrypted EHRs 80 corresponding to the subtree to encrypted data store 24. The revoked participant will, however, continue to be able to access encrypted EHRs 80 that were stored to encrypted data store 24 prior to the revocation.

Figure 10:
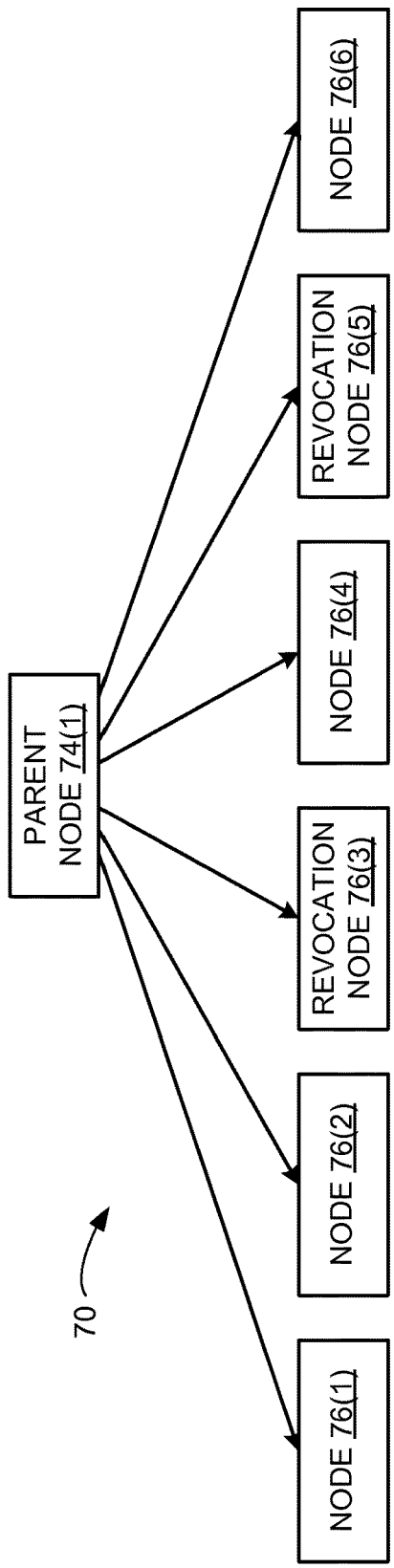
FIG. 10 is a block diagram illustrating one example of a portion of a metadata tree with embedded key revocation information.

FIG. 10 is a block diagram illustrating one example of a portion of a metadata tree 70 with embedded key revocation information. In the example of FIG. 10, two separate key revocations have occurred for a parent node 74(1) as indicated by revocation nodes 76(3) and 76(5). A first version of a node key used to encrypt and decrypt nodes 76(1) and 76(2) was revoked as indicated by a revocation node 76(3), and a second version of the node key used to encrypt and decrypt node 76(4) was revoked as indicated by a revocation node 76(5). A third version of the node key used to encrypt and decrypt nodes 76(6) remains active. When the first version was revoked, the data access adapter 32 performing the first revocation added key rotation information 98 in a parent node 74(1) of the subtree to indicate that the first version of the node key was revoked (e.g., by adding a hash of the first version of the node key to key rotation information 98). Similarly, the data access adapter 32 performing the second revocation added key rotation information 98 in a parent node 74(1) of the subtree to indicate that the second version of the node key was revoked (e.g., by adding a hash of the second version of the node key to key rotation information 98).

In the example of FIG. 10, participant systems 30 that have the first version of the node key may access nodes 76(1) and 76(2) but not nodes 76(4) and 76(6) and may not add new nodes 76 under parent node 74(1). Participant systems 30 that have the second version of the node key may access nodes 76(1), 76(2), and 76(4) but not node 76(6) and may not add new nodes 76 under parent node 74(1). Participant systems 30 that have the third version of the node key may access nodes 76(1), 76(2), 76(4), and 76(6) and add new nodes 76 under parent node 74(1).

To enforce key revocations, data access adapter 32 examines key rotation information 98 in parent node 74(1) to determine whether a node key on participant system 30 has been revoked. For example, data access adapter 32 may determine whether a hash of the node key is in key rotation information 98. If so, data access adapter 32 only allows read access to nodes 76 created prior to the revocation of the node key and does not allow new nodes 76 to be added under parent node 74(1). If not, then data access adapter 32 determines that the node key has not been revoked and allows all nodes 76 to be read and new nodes 76 to be added under parent node 74(1).

In the above embodiments, record keys may be uniquely generated for each encrypted EHR 80 based on a patient key, a provider identifier, and a location of a node 62 in a metadata tree 70 corresponding to the encrypted EHR 80. Each patient key is an encryption key that is unique to a corresponding patient, and each provider identifier represents information that may be used in combination with a patient key to generate a provider key for each patient of the provider. The location represents a fully qualified path in metadata tree 70 (i.e., a uniform resource identifier (URI)). A provider may generate each record key as a function of the provider key and a corresponding location. Patients may generate a record key by accessing the provider identifier and metadata tree 70, generating the provider key using the patient key and the provider identifier, and generating the record key using the provider key and the location of a node 62 in metadata tree 70 corresponding to a desired encrypted EHR 80.

The above embodiments may advantageously support concurrent read and write protocols to a metadata tree journal of a patient while ensuring that participants can reconstruct consistent and up-to-date versions of the metadata tree. The embodiments provide the concurrency without the use of locks to allow the embodiments to be scaled. In addition, the embodiments do not require that the encrypted data store or the metadata store be trusted entities. Further, the embodiments provide a mechanism to revoke access rights as desired.

What is claimed is:

1. A computer implemented method performed by a processing system implemented by at least one hardware processor, the method comprising:

storing in a metadata integrity validator, first integrity information for a metadata tree of a patient, the first integrity information including a summary tree that identifies a state of the metadata tree, the summary tree based on an in-order traversal of a corresponding subtree of the metadata tree, the first integrity information including a hash of the subtree based on a hash function cumulatively applied to nodes of the subtree from a root node to a last node along the in-order traversal;

generating, by the at least one hardware processor, a first reconstructed metadata tree of the patient from a metadata tree journal using the first integrity information to ensure a consistent version is reconstructed from the metadata tree journal, the first reconstructed metadata tree including a plurality of references to a corresponding plurality of encrypted electronic health records of the patient in an encrypted data store;

receiving from the metadata integrity validator, the first integrity information corresponding to the metadata tree journal;

validating the first reconstructed metadata tree by comparing second integrity information of the first reconstructed metadata tree to the first integrity information; and responsive to successfully validating the first reconstructed metadata tree, permitting read and write access to the encrypted data store, comprising:

determining a node in the first reconstructed metadata tree that corresponds to an encrypted electronic health record in the encrypted data store;

accessing the encrypted electronic health record from the encrypted data store using a reference from the node; and decrypting the encrypted electronic health record using a record key.

2. The method of claim 1 further comprising:

accessing the metadata tree journal from a metadata store.

3. The method of claim 1 further comprising:

generating the second integrity information corresponding to the first reconstructed metadata tree subsequent to reconstructing the first reconstructed metadata tree.

4. The method of claim 1 further comprising:

generating the second integrity information as a second hash of the first reconstructed metadata tree; and wherein the first integrity information is a first hash of the metadata tree corresponding to the metadata tree journal.

5. The method of claim 1 further comprising:

generating the first reconstructed metadata tree using the summary tree received from the metadata integrity validator.

6. The method of claim 1 further comprising:

in response to a determination that the first reconstructed metadata tree is not valid, accessing the metadata tree journal from the metadata store;

accessing third integrity information corresponding to the metadata tree journal from the metadata integrity validator;

generating a second reconstructed metadata tree of the patient from the metadata tree journal; and validating the second reconstructed metadata tree by comparing fourth integrity information of the second reconstructed metadata tree to the third integrity information.

7. The method of claim 1 wherein a first one of the plurality of encrypted electronic health records is generated by a first provider, wherein a second one of the plurality of encrypted electronic health records is generated by a second provider, and wherein the second provider is not affiliated with the first provider.

8. A processing system comprising:

a hardware processor; and a memory storing instructions that, when executed by the hardware processor, causes the hardware processor to:

store in a metadata integrity validator, first integrity information for a metadata tree of a patient, the first integrity information including a summary tree that identifies a state of the metadata tree, the summary tree based on an in-order traversal of a corresponding subtree of the metadata tree, the first integrity information including a hash of the subtree based on a hash function cumulatively applied to nodes of the subtree from a root node to a last node along the in-order traversal;

generate a first reconstructed metadata tree from a metadata tree journal provided by a metadata store, wherein the first integrity information is used to generate the first reconstructed metadata tree to ensure a consistent version is reconstructed from the metadata tree journal;

receive the first integrity information from the metadata integrity validator, the first integrity information corresponding to the metadata tree journal;

validate the first reconstructed metadata tree of the patient using the first integrity information received from the metadata integrity validator; and responsive to successful validation of the first reconstructed metadata, permit read and read access to an encrypted data store, including:

determining a node in the first reconstructed metadata tree that corresponds to an encrypted electronic health record in the encrypted data store;

accessing the encrypted electronic health record from the encrypted data store using a reference from the node; and decrypting the encrypted electronic health record using a record key.

9. The processing system of claim 8 wherein the instructions, when executed by the hardware processor, cause the hardware processor to:

access the metadata tree journal from the metadata store;

generate second integrity information from the first reconstructed metadata tree; and validate the first reconstructed metadata tree by comparing the first integrity information to the second integrity information.

10. The processing system of claim 8 wherein the instructions, when executed by the hardware processor, cause the hardware processor to:

generate a second hash of the first reconstructed metadata tree; and validate the first reconstructed metadata tree using the second hash and a first hash of the metadata tree provided by the metadata integrity validator.

11. The processing system of claim 8 wherein the instructions, when executed by the hardware processor, cause the hardware processor to:

generate the first reconstructed metadata tree using the summary tree received from the metadata integrity validator.

12. An article comprising at least one non-transitory machine-readable storage medium storing instructions that, when executed by a processing system, cause the processing system to:

store in a metadata integrity validator, first integrity information for a metadata tree of a patient, the first integrity information including a summary tree that identifies a state of the metadata tree, the summary tree based on an in-order traversal of a corresponding subtree of the metadata tree, the first integrity information including a hash of the subtree based on a hash function cumulatively applied to nodes of the subtree from a root node to a last node along the in-order traversal;

generate a first reconstructed metadata tree from a metadata tree journal provided by a metadata store, wherein the first integrity information is used to generate the first reconstructed metadata tree to ensure a consistent version is reconstructed from the metadata tree journal;

receive the first integrity information from the metadata integrity validator, the first integrity information corresponding to the metadata tree journal;

validate the first reconstructed metadata tree of the patient using the first integrity information received from the metadata integrity validator;

responsive to successful validation of the first reconstructed metadata, permit read and read access to an encrypted data store, including:

providing an encrypted electronic health record to the encrypted data store;

updating the first reconstructed metadata tree in the metadata store to include a first metadata record corresponding to the encrypted electronic health record; and committing the first reconstructed metadata tree to the metadata tree using the metadata integrity validator.

13. The article of claim 12, wherein the instructions, when executed by the processing system, cause the processing system to:

generate second integrity information from the first reconstructed metadata tree;

commit the first reconstructed metadata tree to the metadata tree by providing the first and the second integrity information to the metadata integrity validator.

14. The article of claim 12, wherein the instructions, when executed by the processing system, cause the processing system to:

in response to the first reconstructed metadata tree being rejected by the metadata integrity validator:

generate a second reconstructed metadata tree from the metadata tree journal provided by the metadata store;

validate the second reconstructed metadata tree of the patient using the metadata integrity validator;

provide the encrypted electronic health record to the encrypted data store;

update the second reconstructed metadata tree in the metadata store to include a second metadata record corresponding to the encrypted electronic health record; and commit the second reconstructed metadata tree to the metadata tree using the metadata integrity validator.

15. The article of claim 12, wherein the instructions, when executed by the processing system, cause the processing system to:

determine a location in the first reconstructed metadata tree for the encrypted electronic health record; and generate the metadata record for the location.

16. The article of claim 12, wherein the instructions, when executed by the processing system, cause the processing system to:

encrypt an electronic health record using a record key to generate the encrypted electronic health record.

17. The method of claim 1, wherein:

an initial hash of the subtree corresponds to the hash function applied to the root node, an interim hash of the subtree at each node other than the root node corresponds to the hash function applied to the node and the hash of the subtree at a prior node, and the hash of the subtree corresponds to the interim hash of the subtree at the last node.

18. The method of claim 1, further comprising generating the first integrity information by:

generating a hash of the root node by applying the hash function to the root node, and setting the hash of the subtree to the hash of the root node;

traversing the nodes of the subtree in-order; and while traversing the nodes, at each node after the root node, generating a hash of the node by applying the hash function to the node, and updating the hash of the subtree by applying the hash function to the hash of the node and to the hash of the subtree.

* * * * *